(12) United States Patent
Nakamura et al.

(10) Patent No.: US 6,200,619 B1
(45) Date of Patent: Mar. 13, 2001

(54) PRESERVING AGENT AND PRESERVING METHOD

(75) Inventors: Akihiro Nakamura; Mitsuo Hattori; Hirokazu Maeda, all of Ibaraki (JP)

(73) Assignee: Fuji Oil Co., Ltd., Osaka (JP)

( * ) Notice: Subject to any disclaimer, the term of this patent is extended or adjusted under 35 U.S.C. 154(b) by 0 days.

(21) Appl. No.: 09/379,024

(22) Filed: Aug. 23, 1999

Related U.S. Application Data

(62) Division of application No. 09/011,273, filed on Feb. 10, 1998, now abandoned.

(30) Foreign Application Priority Data

Jun. 17, 1996 (JP) ..................................... 8-155231

(51) Int. Cl.⁷ ............... A23B 4/12; A23B 4/20; A23L 1/0534
(52) U.S. Cl. ............. 426/321; 426/573; 426/618; 426/634
(58) Field of Search .................. 426/321, 573, 426/618, 634

(56) References Cited

U.S. PATENT DOCUMENTS

| 4,927,654 | * | 5/1990 | Barnett et al. ............... 426/573 |
| 5,487,894 | | 1/1996 | Kovacs . |
| 5,700,397 | * | 12/1997 | Maeda et al. ............... 426/654 |
| 5,792,499 | | 8/1998 | Atwell . |
| 6,033,712 | * | 3/2000 | Greenshields et al. ............... 426/573 |

FOREIGN PATENT DOCUMENTS

| 0 521 707 A1 | | 1/1993 | (EP) . |
| 56-109580 | | 8/1981 | (JP) . |
| 57-043668 | | 3/1982 | (JP) . |
| 58-138367 | | 8/1983 | (JP) . |
| 360146828 | * | 12/1983 | (JP) . |
| 60-146823 | | 8/1985 | (JP) . |
| 5-17503 | | 1/1993 | (JP) . |
| 521707 | * | 7/1993 | (JP) . |
| 8-168364 | | 7/1996 | (JP) . |
| 410127250 | * | 5/1998 | (JP) . |

* cited by examiner

Primary Examiner—Helen Pratt
(74) Attorney, Agent, or Firm—Wallenstein & Wagner, Ltd

(57) ABSTRACT

A preserving agent for foods and drinks which contains water-soluble hemicellulose as an effective component, a preserving agent containing (A) water-soluble hemicellulose and (B) one or more selected from the group consisting of ethanol, glycine, glucono-deltalactone, sorbic acid, peroxybenzoic acid, benzoic acid, dehydroacetic acid, hypochlorous acid and their salts, organic acids such as acetic acid, fumaric acid, adipic acid, propionic acid and their salts, lower fatty acid esters, sugar esters, polylysine, protamine, lysozyme, mustard extract, horseradish extract, bleached flour, chitosan and phytic acid as effective components, and a preserving method which employs the preserving agent in food and drink products.

13 Claims, No Drawings

PRESERVING AGENT AND PRESERVING METHOD

RELATED APPLICATION

This application is a divisional of U.S. patent application Ser. No. 09/011,273, filed Feb. 10, 1998, now abandoned upon which a claim of priority is based.

TECHNICAL FIELD

The present invention relates to a preserving agent and to a preserving method.

BACKGROUND ART

Organic acids, inorganic acids, ethanol and glycine are commonly used to prevent degeneration and improve the shelf-life of food products (Japanese Unexamined Patent Publication No. 56-109580, 57-43668, 58-138367).

Various foods have been screened for food-preserving substances in recent years, resulting in the discovery of such preservatives as polylysine, protamine, lysozyme, etc., in addition to synthetic chemical products; however, since these preservatives exhibit exceedingly strong antibacterial activity only against certain specific bacteria, they are not adequate as general food preservatives. In order to achieve satisfactory preservation it is necessary to add large amounts of these substances to foods, which is undesirable because of their high price which increases overall costs.

In addition to these substances, spices which have long been used in foods have also been reported to contain substances exhibiting antibacterial activity, but they also fail to fully satisfy the conditions required for food preservatives.

As mentioned above, preserving agents used in foods and drinks will preferably exhibit a continuous antibacterial effect for preservation over long periods with minimal amounts of addition, and when used in foods they must not impair their taste or texture.

Because widely used food preserving agents such as ethanol, glycine, organic acids and inorganic acids themselves have characteristic flavors and aromas, they cannot be added to foods and drinks in amounts required to provide adequate preservation effects. Also, natural substances such as polylysine, protamine and lysozyme have very weak antibacterial spectra, and thus while exhibiting strong antibacterial activity against specific bacteria they are not effective against most microbes responsible for degeneration of foods, and therefore cannot be considered as satisfactory preserving agents.

DISCLOSURE OF THE INVENTION

As a result of diligent research in the light of these circumstances, the present inventors have found that water-soluble hemicellulose, and especially bean-derived water-soluble hemicellulose, exhibits antibacterial activity and can be effectively employed as a preserving agent for foods and drinks. In particular, water-soluble hemicellulose is effective for foods with water activity (AW) of 0.8 or greater, for example foods such as kneaded marine products (AW=0.8 or greater), raw noodles (AW=0.85) and vegetable salad (AW= 0.9 or greater). When water-soluble hemicellulose is used as a preserving agent for foods and drinks, adequate antibacterial activity should preferably be achieved with only a small amount, and further diligent research by the present inventors has resulted in the finding that using the water-soluble hemicellulose in combination with ethanol, glycine, sorbic acid, benzoic acid and their salts, organic acids such as acetic acid, fumaric acid, adipic acid and their salts, lower fatty acid esters, sugar esters, polylysine, protamine, lysozyme, mustard extract, horseradish extract, chitosan and the like results in notably enhanced antibacterial activity. The present invention has been completed based on these findings.

In other words, the present invention provides preserving agents containing water-soluble hemicellulose as an effective component, preserving agents containing (A) water-soluble hemicellulose and (B) one or more selected from the group consisting of ethanol, glycine, sorbic acid, benzoic acid and their salts, organic acids such as acetic acid, fumaric acid, adipic acid and their salts, lower fatty acid esters, sugar esters, polylysine, protamine, lysozyme, mustard extract, horseradish extract, chitosan and phytic acid as effective components, and a preserving method comprising the combined use of (A) water-soluble hemicellulose and (B) one or more selected from the group consisting of ethanol, glycine, sorbic acid, benzoic acid and their salts, organic acids such as acetic acid, fumaric acid, adipic acid and their salts, lower fatty acid esters, sugar esters, polylysine, protamine, lysozyme, mustard extract, horseradish extract, chitosan and phytic acid.

BEST MODE FOR CARRYING OUT THE INVENTION

The water-soluble hemicellulose according to the present invention is preferably derived from beans, especially soybeans, and particularly from the cotyledon. Also, a lower protein content of the soybean hemicellulose is preferred, and specifically it is preferred to be no greater than 5%.

The water-soluble hemicellulose can be of any molecular weight, but a high molecular substance is preferred, especially an average molecular weight of a few thousand to a few million, and specifically 5000 to one million. If the molecular weight is too large the viscosity will increase, thus lowering the handleability. The average molecular weight of the water-soluble hemicellulose is the value determined by the limiting viscosity method wherein the viscosity of a 0.1 M $NaNO_3$ solution is measured using standard pullulan (product of Showa Denko, KK.) as the standard substance. Measurement of uronic acid was carried out by the Blumenkrantz method and measurement of neutral sugars was carried out by the GLC method after alditol acetation.

The water-soluble hemicellulose is either obtained by water extraction from the hemicellulose-containing starting material or, if necessary, by heat elution under acid or alkali conditions, or it may be eluted by decomposition with an enzyme. The following is an example of a method for producing water-soluble hemicellulose.

Suitable starting materials to be from plants include the husks of oily seeds of soybean, palm, coconut, corn or cottonseed with the oil and protein removed, and lees from grains such as rice or wheat with the starch and other parts removed. If the starting material is soybeans, then okara (bean-curd refuse) which is a by-product from preparation of tofu (bean curd) and soybean milk or separated soybean protein may also be utilized.

These starting materials may be subjected to heat decomposition at a temperature preferably of from 80° C. to 130° C., and more preferably from 100° C. to 130° C., under either acidic or alkali conditions but preferably at a pH near the isoelectric point of each protein, and after fractionation of the water-soluble fraction, it may be dried directly or subjected to activated carbon treatment, resin adsorption treatment or ethanol precipitation to remove the hydrophobic substances or low molecular substances, and then dried to yield the water-soluble hemicellulose. Decomposition extraction may also be carried out with hemicellulase or pectinase.

Water-soluble hemicellulose is a polysaccharide containing galactose, arabinose, xylose, fucose, glucose, rhamnose and galacturonic acid as constituent saccharides. A detailed analysis of the constituents of water-soluble hemicellulose as obtained by hydrolysis may be found in Japanese Unexamined Patent Publication No. 4-325058.

Water-soluble hemicelluloses of large molecular weight have viscosities proportional to their molecular weight, and therefore the viscosity may be used as an index for limiting the suitable range of water-soluble hemicellulose which can be utilized as a preserving agent for foods and drinks. That is, the water-soluble hemicellulose used as a preserving agent according to the invention preferably has a viscosity of 10 mPa.s or greater (measured with a Brookfield rotational viscometer in a 10% aqueous solution at 25° C.), more preferably 50 mPa.s or greater, and even more preferably 80 mPa.s or greater, in a 10% aqueous solution at 25° C. The water-soluble hemicellulose can be used so long as its solution viscosity is less than 1000 mPa.s.

The water-soluble hemicellulose of the invention may be used alone as a preserving agent, or it may be used in combination with one or more known compounds for an improved antibacterial activity. Appropriate substance groups are discussed below.

Ethanol and glycine may be of any grade suitable for addition to food products. Sorbic acid and benzoic acid salts may be either sodium or potassium salts, although potassium salts are preferred. Organic acids such as acetic acid, fumaric acid and adipic acid or their salts may also be of any grade suitable for addition to food products. Lower fatty acid esters to be used may be glycerin esters of caproic acid, caprylic acid, capric acid or lauric acid. Sugar esters used may be any acceptable as food additives. Protamines used may be protamine sulfate or protamine hydrochloride. Mustard extracts or horseradish extracts used may be fat-soluble components of mustard oils. Chitosan is commercially available for common food use, and may be used either in free form or as an acetic acid salt or glutamic acid salt. Phytic acid used may be a commercially available product for common food use.

The amount of the water-soluble hemicellulose to be added to the food or other product will depend on the combination of its constituents and is not particularly restricted, although the preferred range for use is about 0.05 to 15% by weight.

There are no restrictions on the method of adding the preserving agent of the invention, and supplementary substances may be added if so desired or not added if so desired. If added, they may be added to the food or drink product together with the water-soluble hemicellulose, or they may be added separately. If the water-soluble hemicellulose of the invention is to be used in the form of an aqueous solution, it may be sprayed onto the food or drink product, or the product may be immersed in the aqueous solution.

There are no particular restrictions on the timing for addition of the preserving agent, and the water-soluble hemicellulose may be added to the food or drink product by any method desired. Thus, it may be added during any step of the production process for the food or drink, and for example if it is to be added during the processing step, the food or drink may be immersed in the aqueous solution or the aqueous solution sprayed thereon, after heat molding and prior to wrapping.

There are no particular restrictions on the food products to which the preserving agent may be applied, and as examples there may be mentioned grains, fruits, vegetables, seaweed and household dishes or pickled goods containing them as major ingredients, as well as kneaded marine products such as boiled fish paste, chikuwa fish paste, pounded fish cake, fish meat ham and sausage, meat products such as bacon, hamburger and meatballs, soybean milk and tofu, and canned juices and coffee; foods and drinks with water activity (AW) of 0.8 or greater are particularly suitable food products.

Although the mechanism of expression of antibacterial activity by the preserving agent of the invention is not fully understood by the present inventors, the improvement in antibacterial activity will be clearly demonstrated by the examples which follow.

The present invention will now be explained in more detail by way of examples. The water-soluble hemicellulose used in the examples was prepared in the following manner.
Preparation of Water-Soluble Soybean Hemicellulose To raw okara obtained from production of separated soybean protein there was added a 2-fold amount of water, and after adjustment to pH 4.5 with hydrochloric acid, the mixture was heated at 120° C. for 1.0 hour and the water-soluble soybean hemicellulose was extracted. After extraction, the mixture was centrifuged (5000 G×10 min) and the water-soluble fraction containing primarily water-soluble soybean hemicellulose was separated. Sodium hydroxide was added to the aqueous solution containing the water-soluble soybean hemicellulose which was obtained in this manner, and the pH was adjusted to 12. The mixture was then heated at 70° C. for 30 minutes. The precipitate resulting from heating was removed, and the solution was neutralized with hydrochloric acid (pH 7). The resulting water-soluble soybean hemicellulose solution was desalted by dialysis, and after treatment with an activated carbon column, it was dried to prepare water-soluble soybean hemicellulose.

The compositional ratio and sugar composition of the resulting water-soluble hemicellulose were as follows.

| Composition ratio of water-soluble soybean hemicellulose (wt %) | |
|---|---|
| Water | 5.4 |
| Crude protein | 9.1 |
| Crude ash content | 6.3 |
| Polysaccharides | 79.0 |
| Average molecular weight | 207,000 |
| Viscosity[1] | 56.8 |
| Sugar composition of water-soluble soybean hemicellulose (wt %) | |
| Galacturonic acid | 17.6 |
| Rhamnose | 2.6 |
| Fucose | 1.9 |
| Arabinose | 20.5 |
| Galactose | 49.9 |
| Xylose | 6.4 |
| Glucose | 1.1 |

[1]Viscosity: cPs, 10% aqueous solution

EXAMPLE 1

The augmented antibacterial activity achieved by combined use of water-soluble hemicellulose and substances which augment its antibacterial activity was investigated. The antibacterial activity was tested using a standard medium (pH 7.2) with water-soluble hemicellulose at 0%, 0.5%, 1.0% or an adequate amount, and containing substances which augment its antibacterial activity, with *Escherichia coli, Aspergillus oryzae*, Lactobacillus plantarm or Saccharomyces cerevisiae as the bacterial strain. The antibacterial activity was judged by contacting the medium with the bacteria, culturing at 37° C. for 4 days and measuring the resulting turbidity. The turbidity of the medium increases as the bacteria proliferate, and therefore if the test substance has antibacterial activity proliferation of the bacteria will be inhibited, thus limiting the increase in turbidity. The turbidity was measured by determining the absorbance value for visible light at a wavelength of 610 nm (using a PTL-396S spectrophotometer, product of Nihon Spectroscopy), and the units for the turbidity were according to the method of JIS1010. Specifically, the turbidity of water containing 1 ppm kaolin was defined as 1 unit. The results were as follows. The water-soluble hemicellulose was confirmed to have strong preserving power.

\* Antibacterial activity against *Escherichia coli*

| Test group | | Days preserved | | | |
|---|---|---|---|---|---|
| | | 1 | 2 | 3 | 4 |
| No addition | | 152 | 526 | | |
| Water-soluble hemicellulose | 0.5% | 19 | 56 | 268 | 468 |
| ditto | 1.0% | 14 | 45 | 119 | 258 |
| Ethanol alone | 0.05% | 125 | 458 | | |
| ditto | 0.1% | 111 | 415 | 492 | |
| Ethanol + | 0.05% | 42 | 248 | 453 | |
| water-soluble hemicellulose (0.5%) | 1.0% | 9 | 107 | 358 | 472 |
| Glycine alone | 0.5% | 127 | 419 | | |
| ditto | 1.0% | 96 | 398 | 487 | |
| Glycine + | 0.5% | 11 | 47 | 229 | 401 |
| water-soluble hemicellulose (0.5%) | 1.0% | 5 | 22 | 97 | 215 |
| Na ascorbate alone | 0.1% | 108 | 381 | | |
| ditto | 0.5% | 12 | 256 | 418 | |
| Na ascorbate + | 0.1% | 14 | 218 | 436 | |
| water-soluble hemicellulose (0.5%) | 0.5% | 0 | 0 | 18 | 75 |
| Glycerin fatty acid ester alone | 0.01% | 124 | 395 | | |
| ditto | 0.05% | 54 | 250 | 481 | |
| Glycerin fatty acid ester + | 0.01% | 5 | 49 | 293 | 412 |
| water-soluble hemicellulose (0.5%) | 0.05% | 0 | 14 | 52 | 239 |
| Common salt alone | 1.0% | 132 | 500 | | |
| ditto | 2.0% | 10 | 375 | | |
| Common salt + | 1.0% | 18 | 48 | 329 | 500 |
| water-soluble hemicellulose (0.5%) | 2.0% | 8 | 34 | 325 | 500 |
| Horseradish extract alone | 0.1% | 15 | 79 | 176 | 338 |
| ditto | 0.5% | 7 | 18 | 125 | 216 |
| Horseradish extract + | 0.1% | 12 | 28 | 114 | 159 |
| water-soluble hemicellulose (0.5%) | 0.5% | 0 | 0 | 21 | 26 |

\* Antibacterial activity against *Aspergillus oryzae*

| Test group | | Days preserved | | | |
|---|---|---|---|---|---|
| | | 1 | 2 | 3 | 4 |
| No addition | | 289 | 587 | | |
| Water-soluble hemicellulose | 0.5% | 117 | 356 | | |
| ditto | 1.0% | 104 | 245 | 479 | |
| Ethanol alone | 0.05% | 23 | 158 | 398 | |
| ditto | 0.1% | 15 | 115 | 292 | 439 |
| Ethanol + | 0.05% | 12 | 144 | 393 | |
| water-soluble hemicellulose (0.5%) | 1.0% | 9 | 107 | 358 | 472 |
| Glycine alone | 0.5% | 107 | 219 | 428 | |

-continued

\* Antibacterial activity against *Aspergillus oryzae*

| Test group | | Days preserved | | | |
|---|---|---|---|---|---|
| | | 1 | 2 | 3 | 4 |
| ditto | 1.0% | 76 | 178 | 382 | |
| Glycine + | 0.5% | 81 | 127 | 299 | 491 |
| water-soluble hemicellulose (0.5%) | 1.0% | 45 | 132 | 193 | 375 |
| Na ascorbate alone | 0.1% | 121 | 389 | | |
| ditto | 0.5% | 72 | 196 | 478 | |
| Na ascorbate + | 0.1% | 44 | 259 | 498 | |
| water-soluble hemicellulose (0.5%) | 0.5% | 36 | 87 | 298 | 465 |
| Glycerin fatty acid ester alone | 0.01% | 119 | 495 | | |
| ditto | 0.05% | 79 | 275 | 475 | |
| Glycerin fatty acid ester + | 0.01% | 86 | 247 | 453 | |
| water-soluble hemicellulose (0.5%) | 0.05% | 42 | 184 | 352 | |
| Common salt alone | 1.0% | 82 | 418 | | |
| ditto | 2.0% | 62 | 245 | 485 | |
| Common salt + | 1.0% | 54 | 198 | 351 | 500 |
| water-soluble hemicellulose (0.5%) | 2.0% | 32 | 114 | 305 | 500 |
| Horseradish extract alone | 0.1% | 32 | 89 | 224 | 379 |
| ditto | 0.5% | 9 | 27 | 195 | 289 |
| Horseradish extract + | 0.1% | 28 | 68 | 107 | 298 |
| water-soluble hemicellulose (0.5%) | 0.5% | 0 | 29 | 89 | 127 |

\* Antibacterial activity against *Lactobacillus plantarm*

| Test group | | Days preserved | | | |
|---|---|---|---|---|---|
| | | 1 | 2 | 3 | 4 |
| No addition | | 120 | 226 | 418 | |
| Water-soluble hemicellulose | 0.5% | 41 | 159 | 379 | 487 |
| ditto | 1.0% | 24 | 95 | 178 | 352 |
| Ethanol alone | 0.05% | 41 | 254 | 482 | |
| ditto | 0.1% | 11 | 185 | 372 | |
| Ethanol + | 0.05% | 40 | 215 | 311 | |
| water-soluble hemicellulose (0.5%) | 1.0% | 11 | 126 | 343 | 461 |
| Glycine alone | 0.5% | 113 | 329 | | |
| ditto | 1.0% | 71 | 197 | 314 | |
| Glycine + | 0.5% | 25 | 105 | 236 | 417 |
| water-soluble hemicellulose (0.5%) | 1.0% | 46 | 88 | 141 | 274 |
| Na ascorbate alone | 0.1% | 108 | 211 | 362 | |
| ditto | 0.5% | 57 | 129 | 312 | |
| Na ascorbate + | 0.1% | 44 | 119 | 213 | 325 |
| water-soluble hemicellulose (0.5%) | 0.5% | 12 | 23 | 78 | 113 |
| Glycerin fatty acid ester alone | 0.01% | 73 | 291 | | |
| ditto | 0.05% | 49 | 237 | 391 | |
| Glycerin fatty acid ester + | 0.01% | 5 | 53 | 141 | 315 |
| water-soluble hemicellulose (0.5%) | 0.05% | 0 | 29 | 68 | 227 |
| Common salt alone | 1.0% | 97 | 398 | | |
| ditto | 2.0% | 24 | 344 | | |
| Common salt + | 1.0% | 18 | 68 | 122 | 370 |
| water-soluble hemicellulose (0.5%) | 2.0% | 11 | 34 | 97 | 289 |
| Horseradish extract alone | 0.1% | 10 | 41 | 143 | 317 |
| ditto | 0.5% | 7 | 17 | 103 | 205 |
| Horseradish extract + | 0.1% | 9 | 18 | 111 | 201 |
| water-soluble hemicellulose (0.5%) | 0.5% | 0 | 0 | 24 | 36 |

\* Antibacterial activity against *Saccharomyces cerevisiae*

| Test group | | Days preserved | | | |
|---|---|---|---|---|---|
| | | 1 | 2 | 3 | 4 |
| No addition | | 259 | 512 | | |
| Water-soluble hemicellulose | 0.5% | 29 | 66 | 107 | 212 |
| ditto | 1.0% | 17 | 29 | 96 | 147 |
| Ethanol alone | 0.05% | 151 | 458 | | |

-continued

*Antibacterial activity against Saccharomyces cerevisiae*

| Test group | | Days preserved | | | |
|---|---|---|---|---|---|
| | | 1 | 2 | 3 | 4 |
| ditto | 0.1% | 93 | 205 | 418 | |
| Ethanol + | 0.05% | 23 | 42 | 95 | 141 |
| water-soluble hemicellulose (0.5%) | 1.0% | 0 | 13 | 27 | 119 |
| Glycine alone | 0.5% | 89 | 213 | 388 | |
| ditto | 1.0% | 58 | 168 | 301 | 458 |
| Glycine + | 0.5% | 10 | 46 | 97 | 196 |
| water-soluble hemicellulose (0.5%) | 1.0% | 4 | 13 | 54 | 107 |
| Na ascorbate alone | 0.1% | 117 | 386 | | |
| ditto | 0.5% | 48 | 196 | 401 | |
| Na ascorbate + | 0.1% | 12 | 117 | 296 | |
| water-soluble hemicellulose (0.5%) | 0.5% | 0 | 0 | 20 | 95 |
| Glycerin fatty acid ester alone | 0.01% | 102 | 377 | | |
| ditto | 0.05% | 49 | 129 | 391 | |
| Glycerin fatty acid ester + | 0.01% | 5 | 19 | 116 | 208 |
| water-soluble hemicellulose (0.5%) | 0.05% | 0 | 11 | 48 | 171 |
| Common salt alone | 1.0% | 104 | 396 | | |
| ditto | 2.0% | 18 | 359 | | |
| Common salt + | 1.0% | 17 | 46 | 119 | 192 |
| water-soluble hemicellulose (0.5%) | 2.0% | 7 | 28 | 66 | 105 |
| Horseradish extract alone | 0.1% | 10 | 58 | 112 | 154 |
| ditto | 0.5% | 5 | 13 | 75 | 111 |
| Horseradish extract + | 0.1% | 0 | 9 | 18 | 58 |
| water-soluble hemicellulose (0.5%) | 0.5% | 0 | 0 | 11 | 27 |

As the above results show, water-soluble hemicellulose not only naturally exhibited a more excellent preserving effect than no addition, but also compared to substances heretofore known to have antibacterial activity, while the combined use of these antibacterial substances with water-soluble hemicellulose provided still greater preserving effects.

EXAMPLE 2

Each of the preservatives listed below was added to a basic composition prepared by adding 50 g of common salt, 150 g of starch, 15 g of sodium glutamate, 20 g of sugar and 1.5 kg of ice water to 3 kg of frozen ground white fish meat (The respective proportions of each component added with respect to the basic composition are also listed below, in terms of weight percentages.), and after filling 100 g of each composition into a vinylidene chloride film and heating for 30 minutes in hot water at 90° C., it was cooled in running water for 40 minutes to make boiled fish paste rolls. Each test group consisting of 10 fish paste rolls was stored in an incubator at 30° C., and the keeping quality was visually observed to determine the preserving property. The results are listed below.

| Preservative[1] | A | B | C | D | E | F | G | H |
|---|---|---|---|---|---|---|---|---|
| No addition | | | | | | | | |
| 1 (control group) | 0.5 | | | | | | | |
| 2 (control group) | | 0.5 | | | | | | |
| 3 (control group) | | | 0.5 | | | | | |
| 4 (control group) | | | | 0.05 | | | | |
| 5 (control group) | | | | | 0.05 | | | |
| 6 (control group) | | | | | | 0.05 | | |
| 7 (control group) | | | | | | | | 0.5 |
| 8 (example group) | 0.5 | | | | | | | |
| 9 (example group) | 0.5 | 0.5 | | | | | | |
| 10 (example group) | 0.5 | | 0.5 | | | | | |
| 11 (example group) | 0.5 | | | 0.5 | | | | |
| 12 (example group) | 0.5 | | | | 0.05 | | | |
| 13 (example group) | 0.5 | | | | | 0.05 | | |
| 14 (example group) | 0.5 | | | | | | 0.05 | |
| 15 (example group) | 0.5 | | | | | | | 0.5 |

Note 1:
A = water-soluble hemicellulose
B = ethanol
C = glycine
D = sodium ascorbate
E = glycerin fatty acid ester
F = polylysine
G = lysozyme
H = horseradish extract

| | Preservation results | | | | | | | |
|---|---|---|---|---|---|---|---|---|
| | Days preserved | | | | | | | |
| Preservative[1] | 1 | 2 | 3 | 4 | 5 | 6 | 7 | 8 |
| No addition | 2/10 | 10/10 | | | | | | |
| 1 (control group) | 1/10 | 4/10 | 10/10 | | | | | |
| 2 (control group) | 0/10 | 3/10 | 8/10 | 10/10 | | | | |
| 3 (control group) | 1/10 | 4/10 | 7/10 | 10/10 | | | | |
| 4 (control group) | 0/10 | 3/10 | 8/10 | 10/10 | | | | |
| 5 (control group) | 0/10 | 3/10 | 6/10 | 8/10 | 10/10 | | | |
| 6 (control group) | 0/10 | 4/10 | 7/10 | 9/10 | 10/10 | | | |
| 7 (control group) | 0/10 | 0/10 | 1/10 | 2/10 | 5/10 | 6/10 | 10/10 | |
| 8 (example group) | 0/10 | 0/10 | 0/10 | 2/10 | 5/10 | 7/10 | 10/10 | |
| 9 (example group) | 0/10 | 0/10 | 1/10 | 3/10 | 6/10 | 9/10 | 10/10 | |
| 10 (example group) | 0/10 | 0/10 | 0/10 | 2/10 | 4/10 | 7/10 | 10/10 | |
| 11 (example group) | 0/10 | 0/10 | 0/10 | 1/10 | 3/10 | 9/10 | 10/10 | |
| 12 (example group) | 0/10 | 0/10 | 0/10 | 2/10 | 5/10 | 8/10 | 9/10 | 10/10 |
| 13 (example group) | 0/10 | 0/10 | 0/10 | 1/10 | 3/10 | 7/10 | 10/10 | |
| 14 (example group) | 0/10 | 0/10 | 0/10 | 3/10 | 5/10 | 8/10 | 10/10 | |
| 15 (example group) | 0/10 | 0/10 | 0/10 | 0/10 | 2/10 | 4/10 | 7/10 | 10/10 |

As the above results clearly show, the example groups which contained preserving agents according to the invention exhibited high keeping quality. Incidentally, no adverse effects on quality were observed by addition of the preserving agents of the invention.

EXAMPLE 3

A mixture of 500 g of wheat flour, 10 g of common salt and 200 ml of water was worked into a long dough using a roller, and raw noodles were prepared by the conventional method. After further subjecting it to the processing step described below, samples were placed in sterilized petri dishes and covered, and then subjected to a preservation test under conditions of 35° C. temperature, 85% relative humidity.

(A) control group (no addition)

(B) Addition of 1.0% water-soluble hemicellulose during dough mixing (C) Addition of 0.5% water-soluble hemicellulose during dough mixing, with shaping and boiling followed by immersion for 10 seconds in 1.0% aqueous solution of water-soluble hemicellulose and draining.

(D) Preparation of boiled noodles followed by immersion for 10 seconds in 1.0% aqueous solution of water-soluble hemicellulose and draining.

The results of the preservation test were as follows.

| Test group | Storage time | | | | | | |
|---|---|---|---|---|---|---|---|
| | 10 | 20 | 30 | 42 | 66 | 80 | 100 |
| A (control) | − | − | + | + + | | | |
| B (example) | − | − | − | − | + | + + | |
| C (example) | − | − | − | − | − | + | + + |
| D (example) | − | − | − | + | + + | | |

Symbols
−: no change
+: microbe appearance, partial softening
+ +: microbe appearance, partial dissolution These results clearly demonstrate the superiority of example groups (B), (C) and (D) according to the invention.

EXAMPLE 4

Potato salad was prepared with the composition listed below. Samples were prepared with addition of 0.5% water-soluble hemicellulose with and without 0.3% sodium acetate, and two control groups, one with no addition and one with addition of only 0.3% sodium acetate. The test samples were stored at 20° C. and the keeping quality of each compared. The results were as shown below.

| Potato salad composition (parts by weight) | |
|---|---|
| mashed potato | 55 |
| mayonnaise | 15 |
| carrot | 15 |
| cucumber | 10 |
| salt | 1 |
| pepper | 0.5 |

Processing method (A) no addition (B) addition of 0.5% sodium acetate (C) addition of 0.5% water-soluble hemicellulose (D) addition of 0.5% water-soluble hemicellulose and 0.3% sodium acetate

| Preservation results | | | | | |
|---|---|---|---|---|---|
| | Days preserved | | | | |
| Test group | 1 | 2 | 3 | 4 | 5 |
| A (control) | − | + | + + | | |
| B (control) | − | − | + | + + | |
| C (example) | − | − | − | + | + + |
| D (example) | − | − | − | + | + + |

Symbols
−: no change
+: microbe appearance, partial softening
+ +: microbe appearance, partial dissolution These results clearly demonstrate the superiority of the example groups of the invention.

Industrial Applicability

As shown above, preserving agents according to the invention when used in food and drink products exhibit sufficient preserving effects even when added in small amounts, and with boiled fish paste for example, extended storage of the fish paste was possible of up to 5 times longer and without impairing the taste or texture or contributing an undesirable flavor, compared to cases using no preserving agent of the invention. Also, for the storage of boiled noodles, immersion of the boiled noodles in a 1.0% aqueous solution of a preserving agent of the invention inhibited proliferation of microbes, while a preserving effect was also found with 1.0% addition during preparation of raw noodles. Thus, since an adequate preserving effect can be obtained by addition of the preserving agents to raw materials for foods and drinks during their preparation, the preserving agents are also superior in terms of handleability. Furthermore, the preserving agents of the invention can be used in combination with other substances such as ethanol, glycine, lysine and glycerin fatty acid esters for an enhanced preserving effect, and can be used as natural preservatives for cosmetics and pharmaceuticals in addition to food products.

What is claimed is:

1. A method for preserving, comprising adding water-soluble hemicellulose in an amount of at least 0.5% a kneaded marine product, wherein the preservation time of the product with a water activity of 0.8 or greater, when said water-soluble hemicellulose is added, is 72 hours when stored at 30° C.

2. A method according to claim 1, wherein the water-soluble hemicellulose is derived from soybeans.

3. A method according to claim 1, wherein one or more of the group consisting of ethanol, glycine, gluconodeltalactone, sorbic acid, peroxybenzoic acid, benzoic acid, dehydroacetic acid, hypochlorous acid, the salts of hypochlorous acid, acetic acid, fumaric acid, adipic acid, propionic acid, acetic acid salts, fumaric acid salts, adipic acid salts, propionic acid salts, lower fatty acid esters, sugar esters, polylysine, protamine, lysozyme, mustard extract, horseradish extract, bleached flour, chitosan, and phytic acid are added in combination with the water-soluble hemicellulose.

4. A method for preserving, comprising adding water-soluble hemicellulose in an amount of at least 1.0% to a raw noodle product, wherein the preservation time of the product with water activity of 0.8 or greater, when said water-soluble hemicellulose is added, is 66 hours when stored at 30° C. and an 85% relative humidity.

5. A method according to claim 4, wherein the water-soluble hemicellulose is derived from soybeans.

6. A method according to claim 4, wherein one or more of the group consisting of ethanol, glycine, gluconodeltalactone, sorbic acid, peroxybenzoic acid, benzoic acid, dehydroacetic acid, hypochlorous acid, the salts of hypochlorous acid, acetic acid, fumaric acid, adipic acid, propionic acid, acetic acid salts, fumaric acid salts, adipic acid salts, propionic acid salts, lower fatty acid esters, sugar esters, polylysine, protamine, lysozyme, mustard extract, horseradish extract, bleached flour, chitosan, and phytic acid are added in combination with the water-soluble hemicellulose.

7. A method for preserving, comprising adding water-soluble hemicellulose in an amount of at least 0.5% to a vegetable salad product, wherein the preservation time of the product with a water activity of 0.9 or greater, when said water-soluble hemicellulose is added, is 72 hours when stored at 20° C.

8. A method according to claim 7, wherein the water-soluble hemicellulose is derived from soybeans.

9. A method according to claim 7, wherein one or more of the group consisting of ethanol, glycine, gluconodeltalactone, sorbic acid, peroxybenzoic acid, benzoic acid, dehydroacetic acid, hypochlorous acid, the salts of hypochlorous acid, acetic acid, fumaric acid, adipic acid, propionic acid, acetic acid salts, fumaric acid salts, adipic acid salts, propionic acid salts, lower fatty acid esters, sugar esters, polylysine, protamine, lysozyme, mustard extract, horseradish extract, bleached flour, chitosan, and phytic acid are added in combination with the water-soluble hemicellulose.

10. A method for preserving a food or drink product, comprising adding water-soluble hemicellulose a food or drink product in an amount sufficient to have antibacterial activity against *Escheria coli* for at least about 72 hours, when measured by the turbidity of a standard medium at a pH of 7.2 culturing at 37° C. least about four days.

11. A method for preserving a food or drink product, comprising adding water-soluble hemicellulose a food or drink product in an amount sufficient to have antifungal activity against Aspergillus oryzae for at least about 48 hours, when measured by the turbidity of a standard medium at a pH of 7.2 culturing at 37° C. for at least about four days.

12. A method for preserving a food or drink product, comprising adding water-soluble hemicellulose a food or drink product in an amount sufficient to have antibacterial activity against Lactobacillus plantarm for at least about 96 hours, when measured by the turbidity of a standard medium at a pH of 7.2 culturing at 37° C. for at least about four days.

13. A method for preserving a food or drink product, comprising adding water-soluble hemicellulose in an amount sufficient to have antifangal activity against Saccharomyces cerevisiae for at least about 96 hours, when measured by the turbidity of a standard medium at a pH of 7.2 culturing at 37° C. for at least about four days.

\* \* \* \* \*

UNITED STATES PATENT AND TRADEMARK OFFICE
CERTIFICATE OF CORRECTION

PATENT NO. : 6,200,619 B1
DATED : March 13, 2001
INVENTOR(S) : Akihiro Nakamura, Mitsuo Hattori and Hirokazu Maeda It is certified that error appears in the above-identified patent and that said Letters Patent is hereby corrected as shown below:

Column 10,
Line 42, after "0.5%" should appear the word -- to --
Line 63, after the word "with" should appear the word -- a --

Column 12,
Line 2, after the word "hemicellulose" should appear the word -- to --
Line 6, after "37° C." should appear the words -- for at --
Line 8, after the word "hemicellulose" should appear the word -- to --
Line 14, after the word "hemicellulose" should appear the word -- to --
Line 21, the word "antifangal" should be -- antifungal --

Signed and Sealed this

Third day of September, 2002

Attest:

JAMES E. ROGAN
Attesting Officer
Director of the United States Patent and Trademark Office